United States Patent [19]

Kulli

[11] Patent Number: 4,929,241

[45] Date of Patent: May 29, 1990

[54] MEDICAL NEEDLE PUNCTURE GUARD

[76] Inventor: John C. Kulli, 30 Widewaters La., Pittsford, N.Y. 14534

[21] Appl. No.: 228,581

[22] Filed: Aug. 5, 1988

[51] Int. Cl.⁵ .............................................. A61M 5/32
[52] U.S. Cl. .................................... 604/263; 604/110; 604/192
[58] Field of Search ............... 604/110, 162, 192, 198, 604/263

[56] References Cited

U.S. PATENT DOCUMENTS

| | | | |
|---|---|---|---|
| 3,610,240 | 10/1971 | Harautuneian | 604/162 |
| 3,904,033 | 9/1975 | Haerr | 604/162 X |
| 4,160,450 | 7/1979 | Doherty | 604/162 X |
| 4,725,267 | 2/1988 | Vaillancourt | 604/263 X |
| 4,735,618 | 4/1988 | Hagen | 604/198 X |
| 4,795,432 | 1/1989 | Karczmer | 604/198 X |

Primary Examiner—Dalton L. Truluck
Attorney, Agent, or Firm—Peter I. Lippman

[57] ABSTRACT

A small protective guard rides on the shaft of a needle. After the needle has been inserted into a patient to deliver or withdraw fluids, the guard is positioned to form a protective barrier crossing in front of the needle tip. The guard is fashioned to collapse inward in front of the tip when its front portion is advanced past the needle tip. The guard carries sharp blades that engage the needle shaft and prevent the guard from moving forward off the needle once the device is activated. An optional manually operated trigger mechanism deploys the guard automatically.

19 Claims, 2 Drawing Sheets

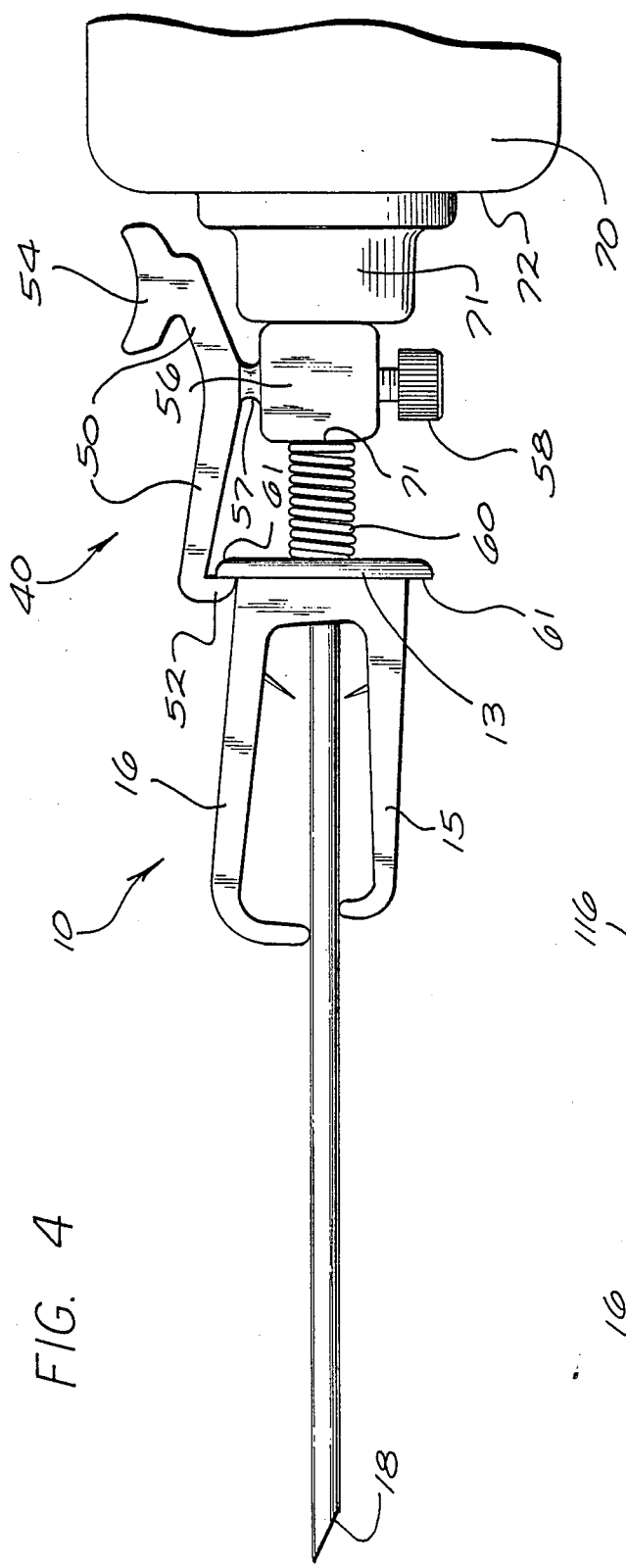
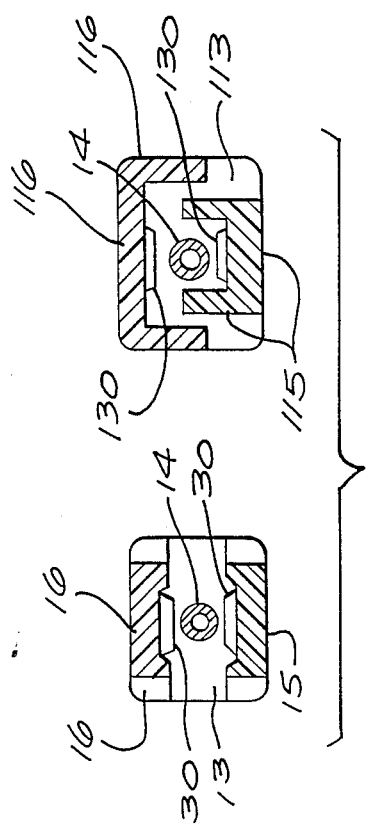
FIG. 4
FIG. 5

MEDICAL NEEDLE PUNCTURE GUARD

BACKGROUND

1. FIELD OF THE INVENTION

This invention relates generally to medical appliances; and more particularly to a safety guard for preventing accidental puncture by a used medical needle.

2. PRIOR ART

As is well known, medical needles serve a myriad of very important medical functions. Throughout the medical community, the severe problem which has developed in relation to use of such needles is also known.

That problem arises from the continuing presence of horrible diseases such as acquired immune deficiency syndrome ("AIDS") and hepatitis, which can be transmitted by exchange of bodily fluids between people. These diseases have led medical institutions to exclusively use disposable needles, syringes and phlebotomy sets to inject medication and to withdraw blood.

A severe residual risk remains, however, for medical personnel themselves in the inadvertent touching of needle tips after withdrawal from infected patients. Medical needles are designed and manufactured specifically to be extremely sharp and to puncture skin and flesh with only the slightest pressure.

As a result, what would ordinarily be an inconsequential scratch or pinprick can bring and has brought severe disease or even death to many medical staff members and others who have become infected after such scratches. Needless to say, health-care professionals are well aware of this risk and take considerable precautions to avoid such inadvertent punctures; thus the risk is reduced on a probability basis to an exceedingly small value.

Nevertheless, the exposure is so massive for working doctors, nurses and technicians that occasional punctures are inevitable. As a practical matter, it is virtually impossible for such an individual to reduce the incidence of accidental puncture to less than, say one every year or perhaps one every few years.

Of course, not every such puncture follows contamination of the needle by a patient carrying a transmissible fatal disease. Nevertheless, there are enough medical personnel and enough such patients that a significant number of medical staffers die—and of course a greater number become very sick—from these accidents.

Sometimes a person using a medical needle has only one hand free to hold the needle prior to properly sheathing it. Since sheathing is most easily performed with two hands, the difficulties inherent in the use of a simple sheathing cap are significant.

Furthermore, possibly ten to twenty percent of needle use occurs in a tense hectic setting or environment where time is short and long laborious precautions can seldom be taken. For instance, learning situations, emergencies and/or a patient's mental or physical condition may complicate needle use. In many situations when other operations need to be performed concurrently, even sheathing can be difficult.

Despite the difficulty, medical staff members who frequently use hypodermic needles and the like have become adept at sheathing needles with one hand. Heretofore this has been the simplest and least problematical solution to a continuing problem.

Nevertheless, the use of sheaths is a very poor solution. The movements involved in sheathing a needle are precisely the kind that sooner or later go astray, leading to an occasional scratch or puncture and thereby statistically to severe illness or death.

Devices which have been introduced to provide added protection against punctures by contaminated hypodermic needles fall into two general design categories. Some devices have protective mechanisms which encase or emanate from the syringe body, while others are associated with the needle itself.

U.S. Pat. No. 4,592,744 to Janine C. Jagger et al. discloses a protective mechanism encasing almost the entire syringe. In this device, the needle is mounted by a relatively tight press fit to the forward end of a syringe that is fitted within a handle. The needle also extends in a relatively loose press fit through a hole in the front of the handle.

After use, the syringe must be pulled bodily out of the back end of the handle, carrying the needle rearward out of its front-end press fit with the handle, and into the cavity within the handle. The needle is carried in a flange that is too wide to escape from the rear end of the handle, and accordingly is pulled away from its tight press fit to the front end of the syringe. Thus the needle is trapped within the handle.

In the phlebotomy device, the blood-collection receptacle is initially enclosed within an outer housing/handle during use. The rear of the needle passes in a tight friction fit through an elastomeric stopper on the receptacle.

Thereafter, the receptacle is used as a tool to unscrew the needle from the forward end of the handle. Then the receptacle stopper, with embedded needle, is pulled off the rear end of the needle so that the receptacle with its blood sample can be removed from the handle.

Thus the two forms of the Jagger invention that are described require the user to perform elaborate compound manipulations including retracting the entire syringe, or double phlebotomy needle, all the way back through the hole in the handle. These maneuvers are all but impossible to accomplish using only one hand. The difficulty will be compounded if the maneuver must be performed with only part of the user's attention, as is often the case.

In most instances the necessary manual operations must include several motions in sequence. What is required is a compound motion, each stage of which is typically of relatively large amplitude in comparison with the length of the needle and the size of the user's hand.

As a matter of ergonomics, the requirement for such large-amplitude and compound motions is inherently adverse to definite, reliable and therefore safe retraction. This is particularly so for medical personnel under harried circumstances.

Other factors, specific to the hypodermic and phlebotomy applications of the Jagger invention, make the procedure even more awkward and difficult. First, as to the Jagger hypodermic needle, proper retraction depends upon maintenance of the design relationships between two friction levels. These relations are too easily upset.

For example, they can be disturbed by temperature variations in storage, beyond the knowledge of the person using the device. They can also be disturbed by leakage of congealable or sticky substances such as blood or sucrose solution, through the large opening at the rear of the handle and into the exposed seams between the handle and the needle flange.

The necessary friction relationships can also be disturbed by imperfect insertion of the syringe tip into its mating receptacle at the rear of the needle flange. That procedure, which in many cases is performed by medical technicians on site, rather than the manufacturer's personnel, can at least in principle damage either of the friction-fitting surfaces involved.

In such circumstances the syringe can be extracted from the needle flange before the needle is retracted—leaving no proper means for retraction.

As to the Jagger phlebotomy needle, the arrangement for retraction is even more adverse to reliable operation. The flange of the phlebotomy needle must actually be unscrewed before it can be pulled back into the handle.

Other prior patents describe devices for automatic or semiautomatic resheathing of hypodermic syringes. U.S. Pat. No. 4,026,287 to Haller is among the better of these devices since it at least provides for retraction of the used needle into a cavity in a unitary, sturdy structure.

That device functions by screwing the plunger into the front of the syringe after use, to destroy a frangible seal that encircles the front of the syringe. Then the needle, which is still attached to the separated front of the syringe, is pulled back by the plunger into the barrel of the syringe. Once again, such elaborate manipulations are problematic in a hurried environment.

Further, Haller's device fails to protect against inadvertent insertion of fingertips into the syringe barrel Even more serious is the fact that Haller's syringe plunger can remain in place, held only by detents at the rear of the barrel. The Haller plunger thus remains dangerously ready to drive the needle forward again if the syringe is accidentally jarred past the detents.

In addition, Haller's device and many of the others discussed below are disadvantageous in that their after-use sheathing configurations are longer than the initial or before-use configurations. When disposed, the longer lengths can be dangerous: they are more susceptible to lateral forces, which cause breakage, than are shorter protective devices.

Mitchell, in U.S. Pat. No. 4,631,057, discloses a device in which a needle guard extends from its retracted position on the syringe body to its activated position around the needle shank. The needle guard is secured in that position by interlocking members. One member is on the needle guard, and the other is on a collar which is mounted to the syringe body.

This device has the disadvantage of leaving the unsealed forward end of the needle guard accessible to fingertips even in the activated position, as with the Haller device. Mitchell's needle guard, however, is more objectionable in this respect since its inside diameter is even larger than that of the syringe. Mitchell's device also shares with the Haller device an undesirable sensitivity to jarring the device out of its safety detents, and an extended after-use configuration.

Other patented devices with a like vulnerability to jarring out of detents and a like extended postuse configuration, but at least providing better frontal shielding against fingertip insertion, are U.S. Pat. Nos. 4,573,976 (Sampson), 4,643,199 (Jennings, Jr. et al.) and 4,643,200 (Jennings, Jr.)

Worthy of mention for its provision of more positive resistance to jarring of the needle out of its retracted position is U.S. Pat. No. 4,425,120 to Sampson et al. That device pays for its better safety locking with complexity of the manual manipulations required in use.

Similar observations apply to U.S. Pat. No. 3,890,971 to Leeson, which offers relatively very compact and stable postuse configuration, but at the cost of a relatively complicated mechanism and large-amplitude motions to effect the resheathing.

Each of these protective mechanisms that are associated with the handle or barrel of a device suffers from a lack of adaptability. Since syringe and phlebotomy devices come in many sizes and shapes, most or all of the protective mechanisms must be specially designed and fitted to the handles or barrels by the manufacturers.

Possibly within the other design category of protective devices—mechanisms associated with the needle rather than the body or barrel—are U.S. Pats. No. 2,876,770 (White), 2,674,246 (Bower) and 3,134,380 (Armao). These devices may appear to provide a protective enclosure for the needle, but they actually provide merely visual shields.

The designs of these shields were aimed mostly at alleviating a patient's fear of an injection. Before use, patients see only the shields. While the needles are still hidden from view, and before the needles actually puncture the skin, the shields apply pressure to the patients in the areas to be pierced. The patients benefit psychologically from concealment of the needles, and physically from the so-called "pressure anesthesia" effect. All this allows the injections to be made more easily.

Although these devices do have housings that enclose the needles, they do not protect against accidental punctures by used needles. In reality, the designs are conducive to such accidental punctures and for the present purposes counterproductive, since they effectively conceal the presence of dangerously sharp and possibly contaminated needles.

One device that provides more than just a visual shield is the ICU High Risk Needle, produced by ICU Medical Inc. Like the visual-shield devices, the ICU unit is associated with the needle rather than the syringe.

The protective sheath is a ribbed cylinder of hard plastic. This cylindrical sheath locks to a plastic sleeve that is snugly fixed along the needle shank.

This design requires a needle whose overall length is over twice that of the usable portion of the needle. The extra length is necessary mostly to accommodate the sheath, and also to provide for a proper locking mechanism of the sheath over the needle.

The locking mechanism consists of an internal flange at the rear of the movable sheath, and a groove formed between two thickened portions of the fixed sleeve. The internally flanged end of the sheath is notched, allowing the flanged end to spread apart and so pass over the thickened portion of the needle.

Once the internal flange is pulled onto the thickened portion, the flange seats in the groove and locks the sheath in place. The ICU device does not directly rely on attachment with the syringe body to function.

The extra needle length makes the ICU needle far more cumbersome than standard needles. In fact, the required lengths become limiting factors in the use of this device. For instance, if a needle with a usable length of five to six inches is required, the needle must be a foot long—usually impractical.

Even when the extra lengths are still within an acceptable range, they are very susceptible to accidental breakage—exposing sharp and jagged steel that is likely contaminated with blood. Such breakage can be caused by laterally applied forces during use and disposal. Moreover, these special and longer needles are not the type generally stocked, which means that they must be made and ordered specially.

Furthermore, the ICU design requires a different sheath length and a different sleeve length, for every needle length. A different sleeve is also required for every needle gauge.

Although needles are in a sense more regular and standardized than syringe and phlebotomy-set barrels and handles, nonetheless needles come in perhaps a thousand combinations of length, gauge, tip configuration, and manufacturer. The ICU strategy is limited to those relatively few needle configurations whose sales volume by a single manufacturer justifies design of molds and fixtures for individually compatible sheaths and sleeves.

Hence the ICU design fails to take effective advantage of the potential for standardization offered by associating the sheath with the relatively featureless needle.

Finally, the protective sheath on the ICU device has a relatively large opening near the needle tip. It provides a protective barrier only by extending approximately one-quarter inch past the needle. Therefore, some people's fingers may still be inserted into the opening.

In summary present protective devices generally are not adaptable to the wide range of syringes and needles which are usually stocked by hospitals and doctor's offices. Also, the majority of devices—both those associated with the syringe and those with the needle—are awkward or impossible to use with one hand, and leave the needle exposed to insertion of fingers through the guard.

SUMMARY OF THE DISCLOSURE

My invention is a safety guard for forming a protective barrier to prevent accidental puncture by a sharp tip of a used needle.

The invention includes some means for mounting the guard for sliding motion along the needle toward the tip. For purposes of generality in expressing my invention I shall refer to these means as the "mounting means."

The guard also has a front portion that is secured to the mounting means, and that includes a transverse shield. When the front portion is advanced past the tip, the shield collapses to form a protective barrier in front of the tip.

The foregoing may be a discussion of my invention in its broadest or most general form. For best enjoyment of the benefits of the invention, however, I prefer to incorporate certain other features or characteristics.

For example, the device of my invention preferably includes some means for locking the guard firmly against forward motion along the needle after the front portion is advanced past the tip. Again for purposes of generality I shall refer to these means as the "locking means." I prefer to include as part of the locking means at least one blade. The blade is carried in the guard. The blade engages the needle to stop forward motion of the guard after the front portion has advanced past the tip.

The front portion of my guard preferably has more than one shield. The shields are advantageously staggered along the length of the needle to form more than one protective barrier in front of the tip.

I prefer to make at least some of the shields opposed, and to place the front portion in contact with the needle. The needle keeps the opposed shields apart, and so prevents the front portion from collapsing before it advances past the tip.

Also, the shields in my invention are preferably spring loaded or otherwise biased against the needle. When the front portion is advanced past the tip, the shields are thus biased together to form the barriers.

Another general or broad form of my invention is a stoppage mechanism to prevent forward motion of a safety device that shields a needle tip.

The mechanism includes sharp blades carried within the device. It also includes some means for biasing sharp edges of the blades against the needle to resist forward motion. These will be called the "biasing means."

When the device is not engaged, the blades point away from the syringe and toward the tip at an angle of roughly thirty degrees from a perpendicular to the needle axis. In this configuration, when the device is engaged, the blades come in contact with the needle and point toward the tip at a smaller angle from the perpendicular.

Further, the blades are angled roughly fifteen degrees from the perpendicular when in contact with the needle.

The blades are mounted so that their angle from the perpendicular decreases with force manually applied in the forward direction, thus pressing outward on the biasing means. Both this greater force level and the sharper blade angle as such contribute to developing a resistive force that increases with any force that is applied manually in the forward direction. The resistive force prevents forward motion after the blades come in contact with the needle.

Another general form of my invention is the combination of a collapsible guard mounted for sliding motion along a needle, and a plurality of razor-sharp blades mounted within the guard. The blades engage the needle and halt forward motion as the guard collapses.

My guard can be much shorter than the desired usable length of the needle. This is an impossible condition for the ICU needle discussed earlier, but readily achieved with my invention whenever the desired usable length of the needle is a half inch or more—which is to say, in most cases.

When the overall guard length is less than the usable needle length, then the overall length of the needle is less than twice its usable length—in most cases, much less.

Furthermore, the construction of my invention is generally independent of needle length and tip configuration (one size fits all) and somewhat insensitive to needle gauge (a few guard gauges accommodate all needle gauges). What is more, the device does not leave the tip accessible to fingertips, and in most cases can be operated with just one hand.

As will be appreciated, these are all enormous advantages.

All of the foregoing operational principles and advantages of the present invention will be more fully appreciated upon consideration of the following detailed description, with reference to the appended drawings.

BRIEF DESCRIPTION OF THE DRAWINGS

FIG. 4 is a side elevation showing a mechanism for automatically deploying the guard.

FIG. 5 is a cross-sectional view showing, on its left-hand side, a protective guard without side panels and on its right-hand side, a guard with side panels.

DETAILED DESCRIPTION OF THE PREFERRED EMBODIMENTS

Figure 1:
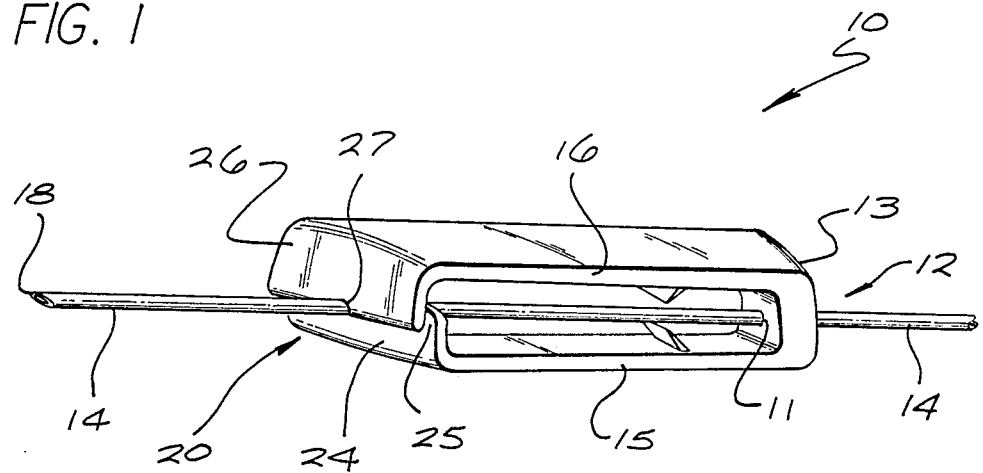
FIG. 1 is a perspective view of an open-sided protective guard before activation.

As shown in FIG. 1 an embodiment of my invention which I now prefer includes a generally rectangular protective guard 10. At the back end 12 of the guard 10 is a transverse wall 13 in which a hole 11 is formed for passage of a needle 14.

Supported at opposite sides of this wall 13 are respective forward-extending jaws 15, 16. For economy of manufacture and reliable operation, the jaws 15, 16 are preferably unitary with the wall 13.

At the front portion 20 of the guard 10—which is to say, at the front ends of the two jaws 15, 16 respectively—are two opposed transverse shields 24, 26. The shields are very strongly spring loaded or otherwise very strongly biased against the needle 14.

Preferably this biasing force is provided by the stiff spring action of the jaws 15, 16 themselves; for this purpose the wall 13, jaws 15, 16 and the shields 24, 26 are formed as a single unitary article from a tough and springy material such as glass-filled nylon. One of these transverse shields 26 is positioned slightly in front of the other 24, so that the shields are staggered lengthwise along the needle 14 as mentioned earlier.

The edges 25, 27 of the shields 24, 26 are thus in contact with and separated by the needle 14 until they are advanced past the needle tip 18. Then, when the shields 24, 26 are no longer separated by the needle 14, the guard 10 collapses forcibly, under the influence of the biasing force described above, to form a protective barrier 29 as shown in FIG. 3.

Although the guard is shown as generally rectangular, other configurations such as a cylinder or a cone could also be suitable. The rectangular shape, is perhaps easiest to illustrate and discuss.

Figure 2:
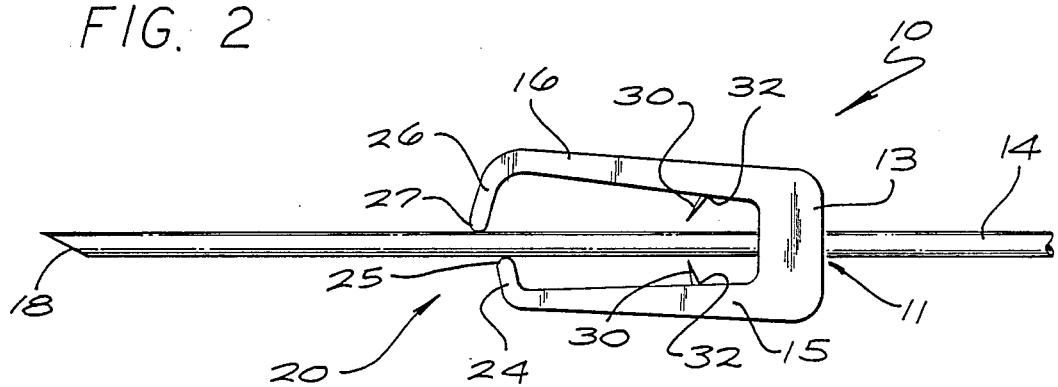
FIG. 2 is a side elevation of the protective guard showing the stopping blades prior to activation.

Razor-sharp blades 30 are hinged 32 in the guard 10 as shown in FIG. 2. As shown, in this nonactivated state the blades 30 are directed forward and are not in contact with the needle 14, while the shield edges 25, 27 are separated by the needle 14.

Figure 3:
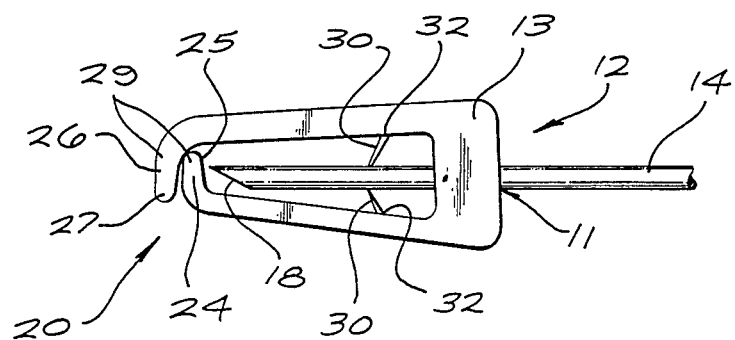
FIG. 3 is a like elevation of the guard in the engaged position.

FIG. 3 shows the protective guard 10 once the front portion 20 is advanced along the needle 14 and past the tip 18. This is the activated mode. The front transverse shields 24, 26 are no longer separated by the needle 14. Instead the front portion 20 has collapsed, disposing the transverse shields 24, 26 to form a protective barrier 29 in front of the needle tip 18. Also, as seen in FIG. 3 the shields 24, 26 are staggered lengthwise along the needle 14. Thus, each transverse shield 24, 26 forms a separate barrier when the front portion 20 collapses.

When the front portion 20 collapses, the blades 30 forcibly engage the needle 14 at an angle of, speaking very roughly, fifteen degrees. The sharpness and hardness of the blades 30 enable them to bite into tiny irregularities, and perhaps even into the crystal structure, of the steel needle 14. The blades 30 thereby firmly and permanently seize the needle 14, preventing further forward motion—while the transverse barrier shields 24, 26 prevent rearward motion. The device is in this way locked on the tip of the needle 18.

Further, the angle of blade contact is such that attempts to move the guard 10 forward result in the blades more forcibly engaging the needle. The hardened steel blades 30 resist breaking and bending.

The blades 30 not only prevent passive forward motion of the protective guard 10 once it has been engaged, but also strongly resist inadvertent or even deliberate application of manual force to move the guard forward. This resistance is particularly effective because forward force on the device produces slight forward motion of the guard, which in turn pivots the blades about their points of engagement with the needle.

The pivoting of the blades opens the jaws very slightly, against the inward-directed spring force—thereby increasing the force applied to bind the blades against the needle. Furthermore, the sharper angle itself increases the effective component of the binding force by changing the magnitude of the cosine effect.

The protective barrier 29 formed by the transverse shields 24, 26 is immune to many of the problems experienced by the devices of the prior art. Most notable is that fingers cannot be inserted axially toward the needle tip 18 once the guard 10 is collapsed.

Additionally, in almost all instances in which a shorter needle is being used—roughly one-and-a-half to two inches—the protective guard 10 can be advanced manually over the needle tip 18 with the thumb of one hand, while that hand continues to grip the body of the syringe or phlebotomy set. This is particularly advantageous when many functions need to be performed concurrently by the person using the needle. When longer needles must be used in procedures, the ability to manipulate the protective guard with one hand can be retained by a simple optional refinement that deploys the guard automatically.

As shown in FIG. 4 that refinement is an attachment which includes a manually operated trigger mechanism 40. The mechanism 40 has a lever 50, that is unitarily joined by a narrow boss 57 to a block 56, which rides on the needle in front of the syringe 70 or needle hub 71. The lever pivots about its flexible attachment 57 to the block 56 and has a large range of radial motion. The block 56 may be fixed along the needle by a set-screw 58.

One end 54 of the lever 50 is fashioned as a button to accommodate a user's thumb or other finger for applying lateral releasing force. The other end 52 is notched to engage a mating structure 61 of the guard 10—preferably near the transverse wall 13 and on the collapsing jaws 15, 16 as shown. For purposes of simplicity, the mating structure 61 is shown as a raised flange. A groove or other engaging structure, however, would also be suitable.

The function of the lever 50 and particularly its notched end 52 is to restrain the guard, counteracting the propulsive force of a compressed spring 60 that is coiled around the needle 14. The spring abuts both the transverse wall 13 of the guard 10 and the block 56.

When lateral force is applied to the lever 50—normally by inward force on the button 54—the lever will pivot (clockwise as shown in FIG. 4) so that the notched end 52 swings outward and no longer restrains the guard 10. This results in the release and transfer of the stored energy of the spring, which causes the guard 10 to be propelled forward to the needle tip 18.

The simplicity and versatility of this device are most apparent when the device is considered for use with a great range of needle lengths and gauges. Most hospitals obtain needles from numerous manufacturers and also stock many different lengths and gauges for varied uses.

Various manufactures may offer over a thousand different combinations of lengths, gauges and needle tip configurations. A relatively few guard gauges, however, will accommodate this entire range of needles. The versatility of these guards is apparent because a small number of stocked sizes will adapt to fit the many species of needles available from manufacturers. Thus needles will not have to be manufactured specially—but rather only ordered approximately one-quarter to three-eighths inch longer than the desired usable length.

One of the great advantages this design has over other devices which are associated with the needle rather than a handle or barrel is that it can be used on very long needles. For instance, in a needle which is seven inches long, a device which engages halfway along the needle and thus needs twice the usable needle length to function would be impractical for use—a needle length of fourteen inches would be required. The present invention, however, will easily fit and function on, say, a seven-and-a-quarter-inch needle, leaving seven inches usable.

Depending on user preference and to some extent on the amount of needle isolation desired, the invention can also be made with side panels 115, 116 as shown on the right-hand side of FIG. 5. The panels 115, 116 extend perpendicularly from opposite sides of the forward-extending jaws 15, 16.

The side panels 115, 116 can be staggered radially out from the needle 14 so that upon activation more than one protective barrier is formed around the shaft of the needle 14—in addition to the barriers formed by the shields 24, 26 over the needle tip 18. For simplicity, the side panels 115, 116 may as shown be unitary with the forward-extending jaws 15, 16.

One difference between the side panels 115, 116 and the shields 24, 26 is that the side panels 115, 116 take a less active role in the activation of the device than do the front shields 24, 26. This is true because unlike the front shields 24, 26 which are separated by and in contact with the needle 14 until the guard 10 is activated, the side panels remain spaced away from the needle 14 in both the nonactivated and activated condition.

This particular configuration 112 having side panels 115, 116 provides a user with maximum protection against contact with blood from a used needle. Blood is most likely to be found residually around the bore in the needle tip 18 and on the shaft 14 near the tip.

It will be understood that the foregoing disclosure is intended to be merely exemplary, and not to limit the scope of the invention—which is to be determined by reference to the appended claims.

I claim:

1. A safety guard for forming a protective barrier to prevent accidental puncture by a sharp tip of a used needle, said guard comprising:
   means for mounting substantially the entire guard for sliding motion along the needle toward the tip; and
   a front portion, secured to the mounting means and comprising a transverse shield, for collapsing to form a barrier in front of the needle tip, when the front portion is advanced past the tip.

2. The guard of claim 1, wherein:
   substantially the entire guard has an overall length that is always less than the usable length of the needle.

3. The guard of claim 1, in further combination with:
   the needle; and
   wherein the needle has an overall length that is less than twice its usable length.

4. The guard of claim 1, wherein:
   substantially the entire guard is always less than one-half inch long.

5. A safety guard for forming a protective barrier to prevent accidental puncture by a sharp tip of a used needle, said guard comprising:
   means for mounting the guard for sliding motion along the needle toward the tip;
   a front portion, secured to the mounting means and comprising a transverse shield, for collapsing to form a barrier in front of the needle tip, when the front portion is advanced past the tip; and
   means for locking the guard directly and firmly to the needle shaft near and behind the tip, against forward motion along the needle, after the front portion is advanced past the tip.

6. A safety guard for forming a protective barrier to prevent accidental puncture by a sharp tip of a used needle, said guard comprising:
   means for mounting the guard for sliding the motion along the needle toward the tip;
   a front portion, secured to the mounting means and comprising a transverse shield, for collapsing to form a barrier in front of the needle tip, when the front portion is advanced past the tip; and
   means for locking the guard firmly against forward motion along the needle after the front portion is advanced past the tip;
   wherein the locking means comprise at least one blade carried in the guard to engage the needle and stop forward motion of the guard after the front portion is advanced past the tip.

7. A safety guard for forming a protective barrier to prevent accidental puncture by a sharp tip of a used needle, said guard comprising:
   means for mounting the guard for sliding motion along the needle toward the tip; and
   a front portion, secured to the mounting means and comprising a transverse shield, for collapsing to form a barrier in front of the needle tip, when the front portion is advanced past the tip;
   wherein the need is in contact with the front portion and prevents that portion from collapsing before advancing past the tip; and
   before the front portion is advanced past the tip, the shield is biased against the needle;
   whereby when the front portion is advanced past the tip, the shield is biased across the front of the needle tip to form said barrier.

8. A safety guard for forming a protective barrier to prevent accidental puncture by a sharp tip of a used needle, said guard comprising:
   means for mounting the guard for sliding motion along the needle toward the tip; and
   a front portion, secured to the mounting means and comprising a transverse shield, for collapsing to form a barrier in front of the needle tip, when the front portion is advanced past the tip;
   wherein the front portion has more than one transverse shield staggered lengthwise along the needle to form more than one protective barrier.

9. The guard of claim 8, wherein:
at least some of the shields are opposed.

10. The guard of claim 9, wherein:
the shields are biased against the needle;
whereby when the front portion is advanced past the tip, the shields are biased together to form said barriers.

11. A safety guard for forming a protective barrier to prevent accidental puncture by a sharp tip of a used needle, said guard comprising:
means for mounting the guard for sliding motion along the needle toward the tip; and
a front portion, secured to the mounting means and comprising a transverse shield, for collapsing to form a barrier in front of the needle tip, when the front portion is advanced past the tip;
wherein the mounting means and front portion are formed from glass-filled nylon;
wherein the guard further comprises jaws interconnecting the mounting means with the front portion; and
wherein the shield is spring loaded against the needle by resiliency of the glass-filled nylon.

12. A safety guard for forming a protective barrier to prevent accidental puncture by a sharp tip of a used needle, said guard comprising:
means for mounting the guard for sliding motion along the needle toward the tip;
a front portion, secured to the mounting means and comprising a transverse shield, for collapsing to form a barrier in front of the needle tip, when the front portion is advanced past the tip;
propulsion means disposed to contact the guard, for propelling the guard along the needle toward the tip;
restraint means, engaged with the guard, for restraining the guard against propulsion by the propulsion means; and
release means, engaged with the restraining means, for releasing the guard from the restraint means for propulsion toward the tip by the propulsion means.

13. The guard of claim 12, wherein:
the release means are activated by a manually operated trigger.

14. A stoppage mechanism to prevent forward motion of a safety device that shields a needle tip, said mechanism comprising:
sharp blades carried within the device; and
means for resistant forward motion by biasing sharp edges of the blades against the needle.

15. The apparatus of claim 14, wherein:
when the device is not engaged, the blades point toward the tip at an angle of roughly thirty degrees from a perpendicular to the needle axis; and
when the device is engaged, the blades come in contact with the needle and point toward the tip at a smaller angle from the perpendicular.

16. The apparatus in claim 15, wherein:
the blades assume an angle of roughly fifteen degrees from the perpendicular when in contact with the needle.

17. The apparatus of claim 15, wherein:
the blades are mounted so that their angle from the perpendicular decreases, developing a resistive force that increases, with force manually applied to the apparatus in the forward direction;
whereby forward motion is effectively resisted after the blades contact the needle.

18. A stoppage mechanism to prevent forward motion of a safety device that shields a needle tip, said mechanism comprising:
sharp blades carried within the device; and
means for biasing sharp edges of the blades against the needle to resist forward motion;
wherein the blades are made of steel.

19. In combination:
a collapsible guard mounted for sliding motion along a needle; and
a plurality of razor-sharp blades mounted within the guard to stop forward motion by engaging and jamming against the needle shaft as the guard collapses.

* * * * *